US011339770B2

(12) United States Patent
Haibach et al.

(10) Patent No.: US 11,339,770 B2
(45) Date of Patent: May 24, 2022

(54) MASK WITH PRIMARY AND SECONDARY AIR DELIVERY

(71) Applicant: KONINKLIJKE PHILIPS N.V., Eindhoven (NL)

(72) Inventors: Richard Thomas Haibach, Verona, PA (US); Jonathan Sayer Grashow, Pittsburgh, PA (US); Lauren Patricia Chodkowski, Pittsburgh, PA (US); Robert William Baiko, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 382 days.

(21) Appl. No.: 16/468,301

(22) PCT Filed: Dec. 8, 2017

(86) PCT No.: PCT/EP2017/081940
§ 371 (c)(1),
(2) Date: Jun. 11, 2019

(87) PCT Pub. No.: WO2018/108715
PCT Pub. Date: Jun. 21, 2018

(65) Prior Publication Data

US 2020/0078545 A1 Mar. 12, 2020

Related U.S. Application Data

(60) Provisional application No. 62/433,286, filed on Dec. 13, 2016.

(51) Int. Cl.
*F04B 19/00* (2006.01)
*A61M 16/00* (2006.01)
(Continued)

(52) U.S. Cl.
CPC ....... *F04B 19/006* (2013.01); *A61M 16/0066* (2013.01); *A61M 16/022* (2017.08); *F04B 43/043* (2013.01); *A61M 16/0683* (2013.01); *A61M 2016/0027* (2013.01)

(58) Field of Classification Search
CPC .............. A61M 16/00; A61M 16/0057; A61M 16/0066; A61M 16/0069; A61M 16/022;
(Continued)

(56) References Cited

U.S. PATENT DOCUMENTS 6,253,764 B1 7/2001 Calluaud
6,349,724 B1 * 2/2002 Burton ................. F04D 25/166 128/204.18
(Continued)

OTHER PUBLICATIONS

International Search Report—PCT/EP2017/081940 filed Dec. 8, 2017.

*Primary Examiner* — Joseph D. Boecker
(74) *Attorney, Agent, or Firm* — Michael W. Haas

(57) ABSTRACT

A respiratory interface device is provided. The respiratory interface device includes a patient interface device, a patient circuit, and a pressure generating assembly. Pressure generating assembly includes a first pressure generating device and a second pressure generating device. Patient circuit includes a reduced conduit.

11 Claims, 6 Drawing Sheets

20 10 34 38 22 39 32 60 24' 24" 50 62 30

(51) Int. Cl.
*F04B 43/04* (2006.01)
*A61M 16/06* (2006.01)

(58) Field of Classification Search
CPC .............. A61M 16/06; A61M 16/0683; A61M 2016/0027; A62B 18/006; A62B 18/045; A42B 3/286; A42B 3/288; F04B 19/006; F04B 43/043
See application file for complete search history.

(56) References Cited

U.S. PATENT DOCUMENTS

| | | | | |
|---|---|---|---|---|
| 7,114,497 | B2 | 10/2006 | Aylsworth | |
| 8,839,791 | B2 | 9/2014 | Allum et al. | |
| 9,517,367 | B2 | 12/2016 | Dwyer et al. | |
| 2006/0096596 | A1* | 5/2006 | Occhialini | A61M 16/16 128/204.18 |
| 2008/0210242 | A1 | 9/2008 | Burk et al. | |
| 2010/0282260 | A1* | 11/2010 | Sung | A62B 7/12 128/205.12 |
| 2014/0261425 | A1* | 9/2014 | Connor | A61M 16/0069 128/204.23 |
| 2015/0059749 | A1* | 3/2015 | Nitta | A61M 16/0003 128/204.18 |
| 2015/0297854 | A1 | 10/2015 | McCracken | |
| 2015/0320958 | A1* | 11/2015 | Metysek | A61M 16/20 128/204.21 |
| 2015/0335851 | A1* | 11/2015 | Cullen | A61M 16/0057 128/204.25 |
| 2016/0089261 | A1 | 3/2016 | Quinn | |

* cited by examiner

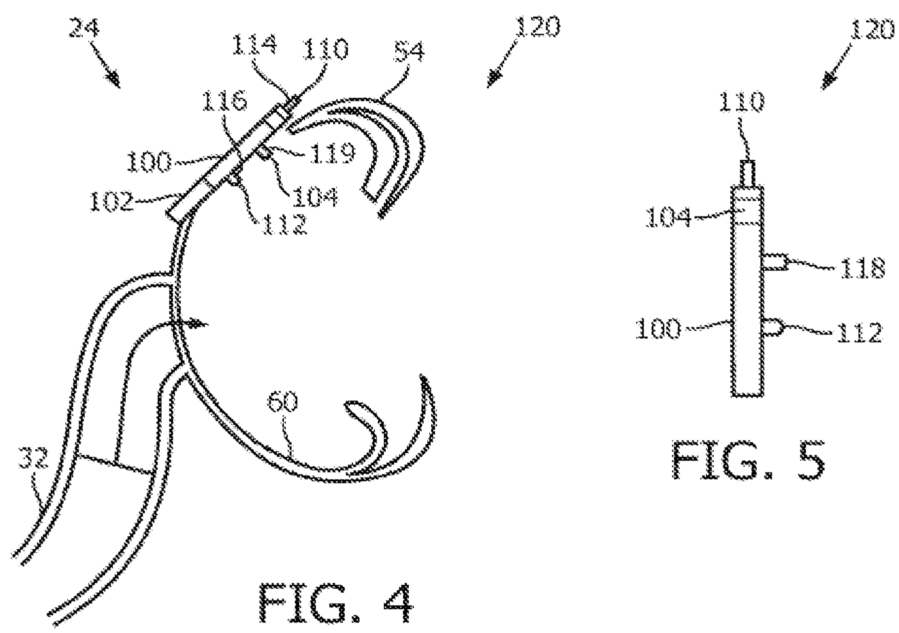
FIG. 4
FIG. 5
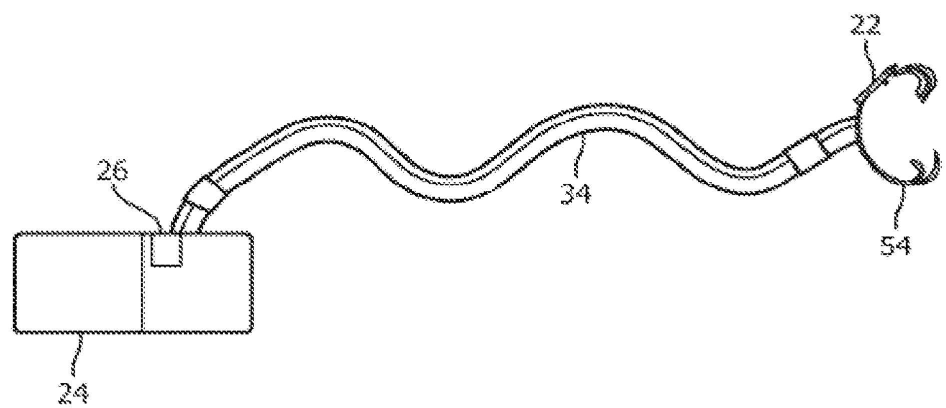
FIG. 6

MASK WITH PRIMARY AND SECONDARY AIR DELIVERY

CROSS-REFERENCE TO PRIOR APPLICATIONS

This application claims the priority benefit under 35 U.S.C. § 371 of International Patent Application No. PCT/EP2017/081940, filed on Dec. 8, 2017, which claims the priority benefit of U.S. Provisional Patent Application No. 62/433,286, filed on Dec. 13, 2016, the contents of which are herein incorporated by reference.

This patent application claims the priority benefit under 35 U.S.C. § 119(e) of U.S. Provisional Application No. 62/433,286 filed on Dec. 13, 2016, the contents of which are herein incorporated by reference.

BACKGROUND OF THE INVENTION

1. Field of the Invention

The present invention relates to respiratory interface devices for transporting a gas to and/or from an airway of a user and, in particular, to a respiratory interface device that includes both primary and secondary air delivery.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient so that a flow of breathing gas can be delivered from a pressure/flow generating device to the airway of the patient. That is, the patient interface device is a part of a respiratory interface device that further includes a patient circuit and a pressure generating device. The pressure generating device is structured to generate a pressure in a fluid, i.e., in normal operation in the atmosphere the pressure generating device generates a flow of air. The patient circuit is structured to couple the pressure generating device to the patient interface device by elements such as, but not limited to, hoses or other conduits. Thus, the pressure generating device is coupled to, and in fluid communication with, the patient interface device via the patient circuit. The hose or conduit conventionally has a diameter of between 15 mm to 22 mm.

A hose or conduit of this size may make the user aware of the hose during use. That is, the hose has a sufficient mass and bulk so that the user may feel the hose during use. Further, use of a smaller diameter hose is not an option because smaller hoses significantly increase the air velocity at a given flow rate. This increase in the air velocity at a given flow rate leads to high noise and a high pressure drop; both of which are undesirable.

Accordingly, a need exists for a respiratory interface device that includes a patient circuit that is less noticeable to the user while not generating high noise and a high pressure drop.

SUMMARY OF THE INVENTION

One embodiment of the presently disclosed concept provides a respiratory interface device including a patient interface device, a patient circuit including a reduced, first conduit a pressure generating assembly including a first pressure generating device and a second pressure generating device. The first pressure generating device is structured to generate a first pressure and the second pressure generating device is structured to generate a second pressure. The first pressure generating device is coupled to, and in fluid communication, with the first conduit. The first conduit is coupled to, and in fluid communication, with the patient interface device. The second pressure generating device is coupled to, and in fluid communication, with the second conduit. The second conduit is coupled to, and in fluid communication, with the patient interface device.

BRIEF DESCRIPTION OF THE DRAWINGS

FIG. 4 is a partially schematic cross-sectional side view of another embodiment of the disclosed concept;

FIG. 5 is a side view of a second pressure generating device housing assembly;

FIG. 6 is a partially schematic isometric view of another embodiment of the disclosed concept.

DETAILED DESCRIPTION OF EXEMPLARY EMBODIMENTS

Figures 1, 1A:
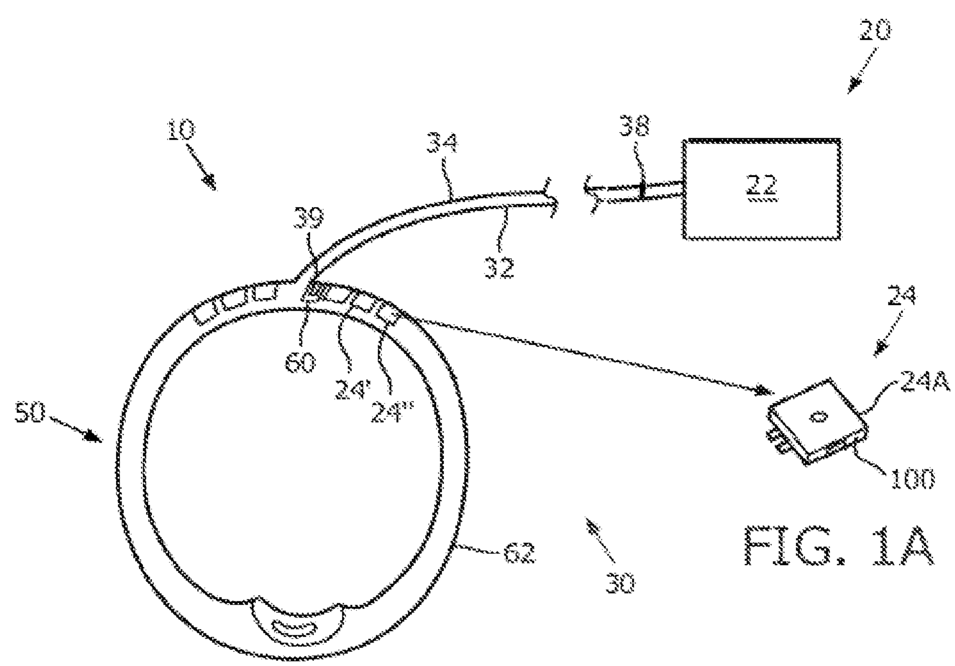
FIG. 1 is a partially schematic isometric view of one embodiment of the disclosed concept.
FIG. 1A is a detail view of a pressure generating device.

As used herein, the singular form of "a," "an," and "the" include plural references unless the context clearly dictates otherwise. As used herein, the statement that two or more parts or components are "coupled shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, a "reduced" hose, conduit, or similar construct, is a construct that is coupled to, and in fluid communication with a patient interface device that is also in fluid communication with two separate pressure generating devices. That is, a "reduced" hose has a smaller diameter relative to a hose in fluid communication with a patient interface device and a single pressure generating device. It is understood that such a hose, in an exemplary embodiment, has a smaller diameter than would be required for a hose operating with a single pressure generating device.

FIGS. 1 and 1A show a respiratory interface device 10. Respiratory interface device 10 includes a pressure generating assembly 20, a patient circuit 30, and a patient interface device 50. Pressure generating assembly 20 includes a plurality of pressure generating devices; as shown, a number of first pressure generating devices 22 and a number of second pressure generating devices 24, it is, however, understood that pressure generating assembly 20 is not limited to two pressure generating devices. For example, as shown in FIG. 1, a plurality of second pressure generating devices 24', 24", which are similar to each other are shown directly coupled to patient interface device 50. In an exemplary embodiment, there is a single first pressure generating device 22 and a plurality of second pressure generating devices 24', 24".

Further, in one embodiment, first pressure generating device 22 is the primary pressure generating device and second pressure generating device 24 is a secondary pressure generating device. That is, as used herein, the "primary" pressure generating device(s) is structured to generate a greater volume of fluid flow relative to a number of "secondary" pressure generating device(s). In one embodiment, primary pressure generating device 22 is coupled to patient interface device 50 by a "reduced" conduit 32 while second pressure generating device 24 is directly coupled to patient interface device 50. In an alternate embodiment, primary pressure generating device 22 is directly coupled to patient interface device 50 while secondary pressure generating device 24 is coupled to patient interface device 50 by reduced conduit 32.

For purposes of the present disclosure, pressure generating assembly 20 includes any device capable of generating a flow of breathing gas or providing gas at an elevated pressure. Examples of such pressure generating systems include a ventilator, CPAP device, or variable pressure device, e.g., an auto-titrating device, proportional assist ventilation (PAV®) device, proportional positive airway pressure (PPAP) device, C-Flex™ device, Bi-Flex® device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device. In an exemplary embodiment, primary pressure generating device 22 is such a device. In an exemplary embodiment, first pressure generating device 22 is structured to generate a pressure of between about 4 cmH2O and 50 cmH2O, and second pressure generating device 24 is structured to generate a pressure of between about 4 cmH2O and 30 cmH2O. Thus, it is noted that the combined flow rate/pressure of first pressure generating device 22 and second pressure generating device 24 generally corresponds to the flow rate/pressure of a prior art pressure generating device.

Figure 2:
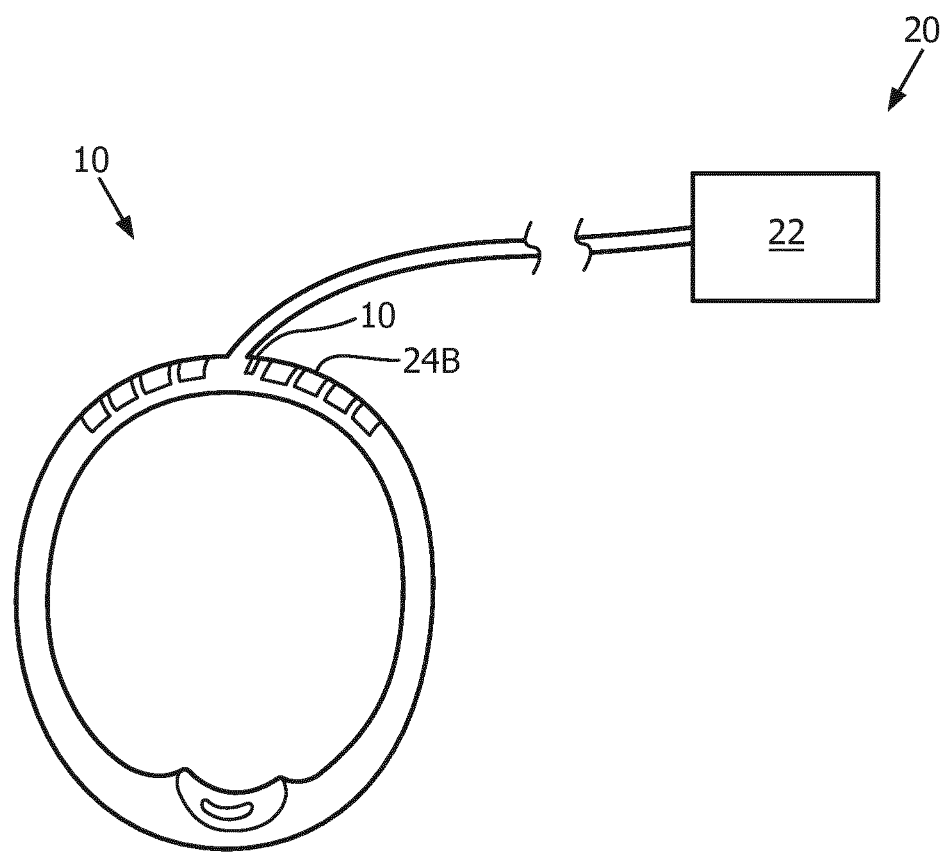
FIG. 2 is a partially schematic isometric view of another embodiment of the disclosed concept.
Figure 3:
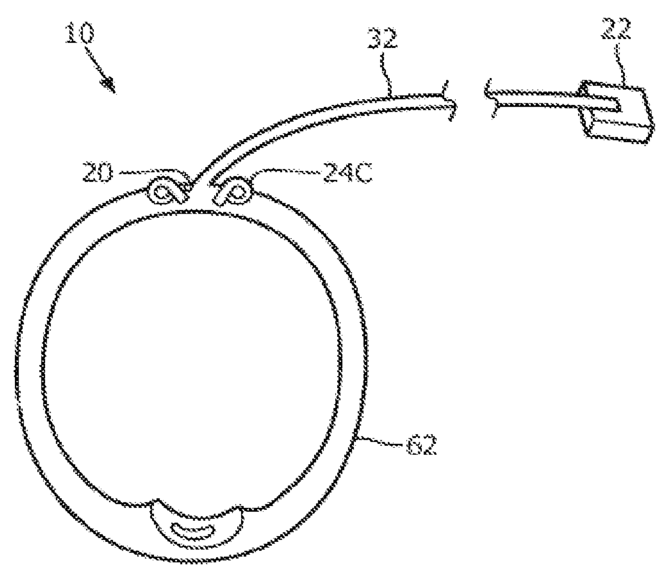
FIG. 3 is a partially schematic isometric view of another embodiment of the disclosed concept.

Second pressure generating device 24, in an exemplary embodiment, is smaller, i.e., second pressure generating device 24 has any of a smaller size, footprint, volume and/or operating characteristics, than first pressure generating device 22 and is coupled, directly coupled, or fixed to patient interface device 50 or to first conduit 32, as discussed below. Second pressure generating device 24 is selected from the group including, or consisting of, a piezoelectric micro blower 24A (FIG. 1), a diaphragm blower 24B (FIG. 2), and a centrifugal blower 24C (FIG. 3).

In one exemplary embodiment, as shown in FIGS. 4-5, second pressure generating device 24 includes a housing assembly 100, a micro-blower 102 (shown schematically), and a pressure sensor 104. Second pressure generating device housing assembly 100 defines a substantially enclosed space (not shown). Second pressure generating device micro-blower 102 is structured to be, and is, disposed in second pressure generating device housing assembly enclosed space. Further, second pressure generating device housing assembly 100 defines an inlet 110 and an outlet 112. Second pressure generating device micro-blower 102 is structured to be, and is, in fluid communication with second pressure generating device housing assembly inlet 110 and second pressure generating device housing assembly outlet 112. Thus, in operation, second pressure generating device micro-blower 102 is structured to, and does, create a fluid flow from second pressure generating device housing assembly inlet 110 to second pressure generating device housing assembly outlet 112. In this embodiment, second pressure generating device housing assembly inlet 110 is second conduit 34, discussed below, and is, in an exemplary embodiment, a first tubular extension 114 on second pressure generating device housing assembly 100. It is noted that second conduit 34 does not have to exist as a visible construct, such as tubular extension 114, but rather second conduit 34 is, in an exemplary embodiment, defined as a passage in housing assembly 100.

Figure 7A:
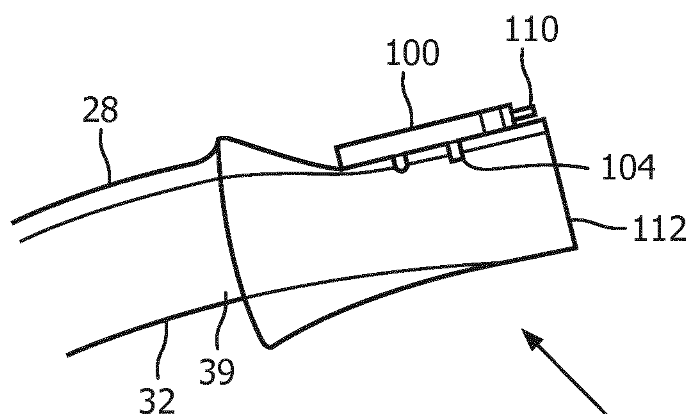
FIG. 7A is a detail view of a second pressure generating device housing assembly.
Figure 7:
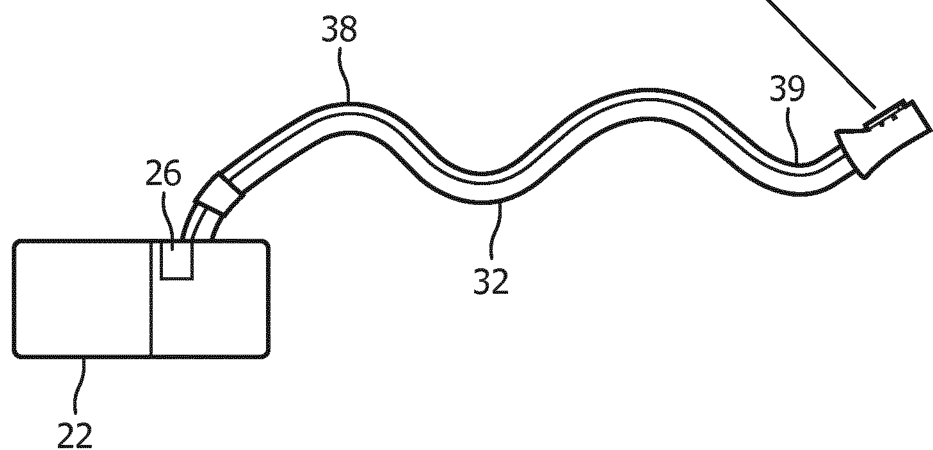
FIG. 7 is a partially schematic isometric view of another embodiment of the disclosed concept.
Figure 8:
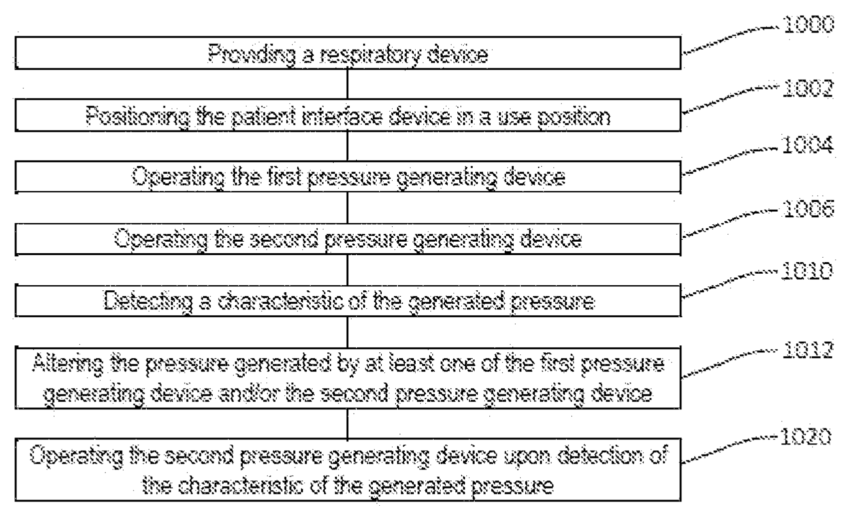
FIG. 8 is a flow chart of the disclosed method.

Further, second pressure generating device housing assembly 100 is structured to be coupled, directly coupled, or fixed to patient interface device 50 or to first conduit 32 (shown in FIGS. 7 and 7A). Second pressure generating device housing assembly inlet 110 is disposed outside of patient interface device interior surface 60 or first conduit 32. Thus, second pressure generating device housing assembly inlet 110 is exposed to the atmosphere. Further, in this embodiment, second pressure generating device housing assembly outlet 112 is a second tubular extension 116 on second pressure generating device housing assembly 100. Second pressure generating device housing assembly outlet 112 is structured to, and does, extend through patient interface device 50 or first conduit 32 so as to provide fluid communication between the area near patient interface device interior surface 60, i.e., within the space defined by the user's face and patient interface device 50, or, interior of first conduit 32.

Further, second pressure generating device housing assembly 100, in an exemplary embodiment, defines a pressure sensor mounting 120. In one embodiment, pressure sensor mounting 120 is a hollow tube 118 structured to, and does, extend through patient interface device 50 or first conduit 32 so as to provide fluid communication between the area near patient interface device interior surface 60 or interior of first conduit 32. In this configuration, pressure sensor 104 is disposed within second pressure generating device housing assembly 100 and is exposed to the fluid pressure adjacent the user's face via pressure sensor mounting 120. In another exemplary embodiment, pressure sensor mounting 120 is a substantially solid member 119 structured to, and does, extend through patient interface device 50 or first conduit 32. In this embodiment, pressure sensor 104 is disposed on pressure sensor mounting 120. If needed, a wire or similar conductor (not shown) extends through pressure sensor mounting 120 to allow for communication between pressure sensor 104 and a control unit (not shown). In another embodiment, pressure sensor 104 is disposed within patient interface device 50 or first conduit 32. As is known, pressure sensor 104 is structured to measure pressure and to produce a signal including data representing the measured pressure.

In this embodiment, pressure generating assembly 20 includes control unit 26 as well as a number of conductors 28. Pressure generating assembly conductors 28 are structured to transmit a current that is used to power second pressure generating device 24 and/or pressure sensor 104, or, to transmit a current that is used to transmit a data signal. Further, in this embodiment, pressure generating assembly conductors 28 extend through patient circuit conduit(s) 32, 34, discussed below. That is, pressure generating assembly conductors 28 are coupled, directly coupled, or fixed to patient circuit conduit(s) 32, 34.

Patient circuit 30 is structured to provide fluid communication between each pressure generating device 22, 24, of pressure generating assembly 20 and patient interface device 50. Patient circuit 30 includes a number of conduits 32, 34 (shown and discussed below), hoses, tubes, pipes, or other constructs that define passages (none shown). At least one of patient circuit conduit 32, 34, (or hoses, tubes, pipes, or other constructs that define passages) is a "reduced" conduit 32, 34 as defined above.

In an exemplary embodiment, patient circuit 30 includes first conduit 32 and second conduit 34. First patient circuit conduit 32 includes a generally flexible, hollow body 36 with a first end 38 and a second end 39. At least one of first conduit 32 and second conduit 34 has a diameter between about 4 mm and 22 mm, or between about 4 mm and 14 mm, or less than 15 mm. Conduits with a diameter that is smaller than the prior art along with a system that provide a total pressure comparable to the prior art solve the problems stated above. It is understood that conduits 32, 34 having a circular cross-section are exemplary and that conduits of any shape are included. That is, as used herein, the recitation of a conduit with a "diameter" also includes any conduit having a cross-sectional area similar to a conduit of the stated diameter.

Further, in an exemplary embodiment, first conduit 32 has a first length and second conduit 34 has a second length. In an exemplary embodiment, the second length is physically shorter than the first length. As used herein, the "physical" length of a conduit means the length when the conduit is extended to a maximum. That is, it is understood that a conduit may be made from a flexible material that can be bent, coiled, or otherwise manipulated so as to have a length that is shorter than the maximum length. Thus, the "physical" length of a conduit means the length when the conduit is extended to a maximum. In an exemplary embodiment, second conduit 34 has a second length of between about 0.0 inches to 24.0 inches. As used herein, when a pressure generating device housing assembly is directly coupled to patient interface device 50, the second length is always zero; this is true even if second pressure generating device housing assembly 100 includes a tubular extension 116 as second pressure generating device housing assembly outlet 112. In the alternative embodiment, first pressure generating device 22 is directly coupled to patient interface device 50 and first conduit 32 has a first length of about 0.0 inches while second conduit 34 is a reduced conduit as defined above. It is noted that a conduit having a length that is smaller than a prior art hose solves the problems stated above.

Patient interface device 50 is shown as a nasal interface device. It is understood, however, that patient interface device 50 can include, without limitation, an oral/nasal mask, nasal pillows, or any other device that provides a suitable gas flow communicating function. Thus, as used herein, the term "patient interface device" shall refer to any of such devices. Patient interface device 50 is coupled to, and in fluid communication with, pressure generating assembly 20 via patient circuit 30. That is, patient interface device 50 is coupled to, and in fluid communication, with first conduit 32 and patient interface device 50 is coupled to, and in fluid communication, with second conduit 34. Further, as discussed above, second conduit 34 is, in one embodiment, incorporated into second pressure generating device 24 which is coupled, directly coupled, or fixed to patient interface device 50 or first conduit 32.

Patient interface device 50 includes an interior surface 60. As shown, in a nasal interface device, patient interface device interior surface 60 is within a number of hollow tubes 62 that are structured to, and do, extend from first conduit 32 to an area adjacent a user's nose. In an oral/nasal mask 54 (FIG. 7) patient interface device interior surface 60 is the surface of patient interface device 50 on an inner surface of a concave mask. In an exemplary embodiment, patient interface device 50 includes a pressure sensor.

In another exemplary embodiment, patient circuit conduit 32 extends from first pressure generating device 22 to second pressure generating device 24. That is, first pressure generating device 22 is in direct fluid communication with second pressure generating device 24. As used herein, "direct fluid communication" between two pressure generating devices means that a fluid moves from an upstream pressure generating device to a downstream pressure generating device without passing through another construct, such as, but not limited to, a patient interface device. In an exemplary embodiment, of this configuration, primary, first pressure generating device 22 is not directly coupled to patient interface device 50, but rather is coupled thereto by a reduced conduit 32. Further, as before, secondary, second pressure generating device 24 is directly coupled to patient interface device 50. That is, for example, first pressure generating device 22 is disposed at a remote location, such as, but not limited to a nightstand, and is coupled to, and in fluid communication with, second pressure generating device 24 via reduced conduit 32. Second pressure generating device 24 is directly coupled to, and is in fluid communication with, patient interface device 50. It is understood that fluid provided by first pressure generating device 22 passes through, and is combined with, the fluid generated by second pressure generating device 24. In an alternate embodiment, primary, first pressure generating device 22 is directly coupled to patient interface device 50 and secondary, second pressure generating device 24 is disposed at a remote location and coupled to first pressure generating device 22 via reduced conduit 32.

In view of the above, a method of using a respiratory interface device 10, as described above, includes: providing 1000 a respiratory interface device 10, positioning 1002 patient interface device 50 in a use position, operating 1004 first pressure generating device, and operating 1006 second pressure generating device. As used herein, a "use position" is a position wherein the respiratory interface device 10 is structured to deliver a gas to a user. In an exemplary embodiment, when in the "use position" patient interface device 50, or a portion thereof, is generally sealed against the user's skin. Providing 1000 respiratory interface device 10 includes patient interface device 50, patient circuit including first conduit 32 and second conduit 34, and pressure generating assembly 20 including first pressure generating device 22 and second pressure generating device 24, first pressure generating device structured to generate a first pressure, second pressure generating device structured to generate a second pressure, first pressure generating device coupled to, and in fluid communication, with first conduit, first conduit coupled to, and in fluid communication, with the patient interface device, second pressure generating device coupled to, and in fluid communication, with second conduit, second conduit coupled to, and in fluid communication, with patient interface device.

In an exemplary embodiment, respiratory interface device 10 includes a control assembly (not shown). Control assembly is structured to receive a signal from pressure sensor 104. Further, control assembly is structured to alter the operation of first and second pressure generating devices 22, 24. Accordingly, operating 1004 first pressure generating device 22 and operating 1006 second pressure generating device 24 include detecting 1010 a characteristic of the generated pressure and altering 1012 the pressure generated by at least one of first pressure generating device 22 and operating 1006 second pressure generating device 24. As used herein, a "characteristic of the generated pressure" includes, but is not limited to, the total pressure generated by first pressure generating device 22 and operating 1006 second pressure generating device 24. In an exemplary embodiment, first pressure generating device 22 operates continuously while second pressure generating device 24 operates 1020 upon detection of a selected characteristic of the generated pressure.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory interface device comprising:

a patient interface device;

a patient circuit;

a pressure generating assembly including a number of first pressure generating devices and a number of second pressure generating devices, wherein the number of first pressure generating devices is/are structured to generate a first pressure from a surrounding atmosphere and the number of second pressure generating devices is/are structured to generate a second pressure from the surrounding atmosphere, wherein the generating of the first pressure and the generating of the second pressure are configured to occur simultaneously;

wherein the first pressure and the second pressure are different;

wherein the number of first pressure generating devices are coupled to the patient interface device by a first conduit of the patient circuit; and wherein the second pressure generating devices are directly coupled to, and in fluid communication with one of the patient interface device or the first conduit.

2. The respiratory interface device of claim 1, wherein the first conduit has a diameter of between about 4 mm and 14 mm.

3. The respiratory interface device of claim 1, wherein the first conduit has a diameter of less than 15 mm.

4. The respiratory interface device of claim 1, wherein:

the number of first pressure generating devices have a first set of operating characteristics;

the number of second pressure generating devices have a second set of operating characteristics; and the second set of operating characteristics is less than the first set of operating characteristics.

5. The respiratory interface device of claim 1, wherein:

the pressure generating assembly includes a number of conductors; and wherein the conductors are directly coupled to the first conduit.

6. The respiratory interface device of claim 1, wherein the number of second pressure generating devices are selected from the group including a piezoelectric micro blower, a diaphragm blower, and a centrifugal blower.

7. The respiratory interface device of claim 1, wherein:

the number of first pressure generating devices have a first set of operating characteristics;

the number of second pressure generating devices have a second set of operating characteristics; and the first set of operating characteristics is less than the second set of operating characteristics.

8. The respiratory interface device of claim 7, wherein:

the first conduit has a first length;

a second conduit of the patient circuit has a second length; and wherein the second length is physically shorter than the first length.

9. A method of using a respiratory interface device comprising:

providing a respiratory interface device including a patient interface device, a patient circuit including a first conduit and a second conduit, and a pressure generating assembly including a first pressure generating device and a second pressure generating device, the first pressure generating device structured to generate a first pressure from a surrounding atmosphere, the second pressure generating device structured to generate a second pressure from the surrounding atmosphere, the first pressure generating device coupled to, and in fluid communication, with the first conduit, the first conduit coupled to, and in fluid communication, with the patient interface device, the second pressure generating device coupled to, and in fluid communication, with the second conduit, the second conduit coupled to, and in fluid communication, with the patient interface device;

positioning the patient interface device in a use position;

operating the first pressure generating device; and operating the second pressure generating device to generate the second pressure while the first pressure generating device generates the first pressure.

10. The method of claim 9, wherein operating the first pressure generating device; and operating the second pressure generating device include:

detecting a characteristic of the pressure generated by operating the first pressure generating device and the second pressure generating device; and altering the pressure generated by at least one of first pressure generating device and the second pressure generating device.

11. The method of claim 9, wherein operating the first pressure generating device; and operating the second pressure generating device include:

operating the number of first pressure generating devices continuously; and operating the number of second pressure generating devices upon detection of a selected characteristic of the pressure generated by operating the first pressure generating device and the second pressure generating device.

* * * * *